(12) United States Patent
Brewster et al.

(10) Patent No.: US 8,454,903 B2
(45) Date of Patent: Jun. 4, 2013

(54) ASSAY DEVICE FOR LIQUID SAMPLE

(75) Inventors: Barry Sinclair Brewster, Royston Herts (GB); Adrian Leslie Walker, St. Neots (GB); Robert John Davies, Cambridge Cambs (GB)

(73) Assignee: Alere Switzerland GmbH, Zug (CH)

( * ) Notice: Subject to any disclaimer, the term of this patent is extended or adjusted under 35 U.S.C. 154(b) by 609 days.

(21) Appl. No.: 10/519,525

(22) PCT Filed: Jun. 26, 2003

(86) PCT No.: PCT/GB03/02765
§ 371 (c)(1),
(2), (4) Date: Aug. 29, 2005

(87) PCT Pub. No.: WO2004/003559
PCT Pub. Date: Jan. 8, 2004

(65) Prior Publication Data
US 2006/0029924 A1    Feb. 9, 2006

(30) Foreign Application Priority Data
Jun. 27, 2002 (EP) .................................. 02254517

(51) Int. Cl.
*G01N 33/00* (2006.01)
(52) U.S. Cl.
USPC ........... 422/401; 422/402; 422/420; 422/421; 422/68.1
(58) Field of Classification Search
USPC ................. 422/50, 55, 56, 99, 401, 402, 420, 422/421, 68.1
See application file for complete search history.

(56) References Cited

U.S. PATENT DOCUMENTS

| | | | |
|---|---|---|---|
| 4,705,513 A | 11/1987 | Sheldon et al. | 604/361 |
| 5,075,078 A | 12/1991 | Osikowicz et al. | 422/56 |
| 5,110,550 A | 5/1992 | Schlipfenbacher et al. | 422/56 |
| 5,468,648 A * | 11/1995 | Chandler | 436/518 |
| 5,602,040 A | 2/1997 | May et al. | 436/514 |

(Continued)

FOREIGN PATENT DOCUMENTS

| EP | 0 421 294 | 9/1995 |
|---|---|---|
| EP | 0 560 411 | 7/2000 |
| WO | 98/22824 | 5/1998 |
| WO | 03/023371 | 3/2003 |

OTHER PUBLICATIONS

International Search Report, PCT/GB03/02765 Completed on Nov. 14, 2003.

*Primary Examiner* — Sam P Siefke
(74) *Attorney, Agent, or Firm* — Foley Hoag LLP

(57) ABSTRACT

Disclosed is an assay device comprising liquid transport means adapted to take up a liquid sample and conduct the liquid to an analyte detection region operable to provide a test signal indicative of the presence and/or amount of an analyte in the liquid sample; the assay device further comprising a sample presence signal generation means, which is not generated by means of an immunoreaction. This sample presence signal generation means can comprise a colored portion, which is overlaid by a material (e.g. nitrocellulose) that is opaque, when dry, and translucent or transparent, when wet, to allow the colored portion to become visible to the user. In another embodiment the signal generation means comprises a color changing material which under-goes a change in its visible properties upon wetting (eg. pH indication). A third embodiment uses a mobilisable detectable which, when wetted by the sample, is carried along resulting in a streaked line parallel with the flow direction.

3 Claims, 5 Drawing Sheets

U.S. PATENT DOCUMENTS

| | | | |
|---|---|---|---|
| 5,622,871 A | 4/1997 | May et al. | 436/514 |
| 5,656,503 A | 8/1997 | May et al. | 436/514 |
| 6,187,598 B1 | 2/2001 | May et al. | 436/514 |
| 6,228,660 B1 | 5/2001 | May et al. | 436/514 |
| 2001/0008774 A1 | 7/2001 | May et al. | 436/514 |
| 2001/0041368 A1 | 11/2001 | May et al. | 436/514 |
| 2003/0049167 A1 | 3/2003 | Jerome et al. | 422/58 |
| 2003/0157699 A1 | 8/2003 | Jerome et al. | 435/287.2 |

* cited by examiner

ASSAY DEVICE FOR LIQUID SAMPLE

FIELD OF THE INVENTION

The invention relates in general to the field of assay devices for measuring an analyte in a liquid sample and, more particularly, to such assay devices having a sample presence signal generation means.

BACKGROUND TO THE INVENTION

A number of assay devices for use in the measurement of one or more analytes in a liquid sample are known. Some of these are complex devices for use by trained personnel; for example, sampling devices for industrial liquids, water etc. or laboratory tests on blood, urine and the like. However, an important category of assay devices includes those intended for home use by consumers, for example home pregnancy test kits. Home pregnancy test kits typically function by determining the amount of the hormone human chorionic gonadotrophin (hCG) in a urine sample, and normally provide a visible indication as to whether a subject is pregnant.

The specific example of the Clearblue test from Unipath, England (Clearblue is a registered Trade Mark) as described in EP 291194 and EP 560411 will now be used to illustrate various issues concerning such devices, although the issues are applicable to a broad class of assay devices.

EP 291194 discloses a lateral flow assay device whereby sample is introduced onto a porous carrier such as nitrocellulose which has been pretreated with a mobilisable labelled first species such as an antibody capable of binding with the analyte of interest. The labelled analyte-antibody complex then permeates into an analyte detection region whereupon it reaches a second species (antibody), immobilised on the porous carrier, which binds the complex. Typically the second species is immobilised in a stripe across the carrier such that, in the presence of analyte, a test signal in the form of a line will appear in the analyte detection region due to concentrating of the label, typically gold or dyed latex.

Such assay devices are used amongst others by users wishing to tell whether they are pregnant, i.e. to detect the presence of the pregnancy hormone hCG. Such users may be using the assay device for the first time or may be a highly emotional state. Furthermore, the test will normally be carried out and interpreted by someone who typically will not be clinically trained. Thus, it is advantageous to have an assay device which is both accurate and reassuring to the user, providing as little ambiguity as possible.

In order to ascertain whether the assay has been carried out properly, a control region is typically present. For example, in EP 291194, an immobilised species is present which is able to bind to the labelled first species. Thus, the control region serves to indicate that in the absence of a positive result, the assay device was both functioning properly and used correctly. It thus indicates that enough sample had been added and that the labelled species was present and was able to permeate along the porous carrier, i.e. that there are no blockages or manufacturing defects etc. The control region is typically downstream of the test region. However, the strength of the signal formed at the control region will depend upon the level of analyte present. A high level of analyte will arguably bind more of the mobilised species leaving less unbound species to reach and bind at the control line.

EP 355244 (Abbott Laboratories) discloses such a control region (e.g. denoted by reference numeral 32 in FIG. 1c) which is configured as a minus sign (see claim 3 and FIGS. 1b and 1c) perpendicular to the direction of flow. The minus sign is also designed to bisect the read (vertical) line such that, in the absence of analyte, only a minus sign is formed, and in the presence of analyte, a plus sign is formed.

However, there are drawbacks with using this approach, one of which is that when using a capture zone such as a line disposed parallel to the direction of flow, binding of the labelled species takes place preferentially at the leading front edge. A strong signal will be observed at the "beginning" of the line which will fade out along its length. This is undesirable from the point of view of a consumer, as the consumer will want to be reassured by the presence of a bold and unambiguous line.

As an alternative, EP 421294 discloses an offset symbol (see FIG. 6). In such an embodiment the test signal and control signal are produced at an angle (denoted by reference letter "C" in FIG. 6) to the direction of fluid flow overcoming the problem of signal fade out. This however is something of a compromise since an offset cross may not be instantly recognisable as a "plus" sign indicative of a positive result, nor would an angled line be necessarily recognisable as a "minus" sign indicative of a negative result.

In the case of EP 291194, the control signal may be a line perpendicular to the direction of flow, which resembles the test signal. In the presence of analyte, two vertical lines are seen. However, in the absence of analyte, only the control signal line is seen, i.e. no visible signal is formed in the analyte detection region. The inventors have found that the absence of a line of any sort in the analyte detection region, following performance of the assay, is undesirable to consumers.

SUMMARY OF THE INVENTION

As an alternative to EP 291194 and related devices, the assay device of the present invention provides a sample presence signal generation means instead of or as well as a control signal generation means. Preferred embodiments provide a way to give a visible signal in the plus/minus format or other formats, including but not limited to those formats where the test signal and a further signal interact to form a specific symbol free from signal fadeout without having to resort to character offset. The signal is generated solely as a consequence of the carrier being wetted by sufficient liquid sample, namely when taken alone is not indicative of a valid negative result since it provides no indication that the test has functioned properly other than that it has been wetted by sufficient liquid sample. Thus the sample presence signal generation means of the present invention functions in a different way to a control signal generation means of the type disclosed in the prior art. In particular, the resulting sample presence signal does not provide information as to whether a labelled antibody (which has a role in forming a test and/or control signal) has been mobilised and permeated along a carrier, nor whether a labelled antibody is functioning correctly (eg that a particular specific binding property has been conserved). The sample presence signal generation means may be positioned anywhere along the carrier although preferably it is positioned downstream from it or more preferably within the analyte detection region.

A conventional control signal generation means is preferably present in addition, distantly located from a test signal (e.g. in the form of a read line) and sample presence signal (e.g. in the form of a sample indicator line).

A preferred embodiment of the invention enables a sample presence indicator line to be disposed parallel to the direction of flow of the sample without signal diminishment since the sample presence signal line is not formed by an immunoreation.

Finally, even in the absence of analyte, the user will still be able to see a sample presence signal, such as a minus sign, as opposed to not seeing any visible signal in the analyte detection zone as provided by EP291194.

According to a first aspect of the present invention there is provided an assay device comprising liquid transport means such as a porous carrier adapted to take up a liquid sample and conduct the liquid to an analyte detection region operable to provide a test signal indicative of the presence and/or amount of an analyte in the liquid sample; characterised in that the assay device further comprises a sample presence signal generation means.

Preferably, the sample presence signal generation means generates a sample presence signal in the analyte detection region.

Preferably, also or instead, the sample presence generation means generates a sample presence signal which interacts with the test signal in the presence of analyte to form an interactive symbol representative of a positive result.

In this specification, the term "immunoreaction" refers to specific binding reactions between an antigen and an antibody. Antibodies include proteins designed to bind to antigens and produced by an animal's immune system or synthetic immune system technologies such as phage display or ribosome display, and includes single chain variable fragments, Fab fragments and other peptides derived from antibodies.

The term "control" as used herein refers to a signal which indicates that a valid assay result has been achieved. Thus, it must indicate that one or more of the reagents, which have a role in providing the test and/or control signals, are present in functional form. An example of such a control is given in EP 0560411, wherein the control zone contains immobilised antibody or analyte that can bind to the labelled reagent.

The term "interactive symbol", when applied to the test signal and sample presence signals, means that the two signals together form a symbol which a user will typically understand as an indicator having a semantic meaning as a whole. For example, if the test signal and sample presence signal together form a cross, this will be perceived as a single symbol having its own semantic meaning: a positive result. Even if the two signals are not directly in contact, they may still interact if they are sufficiently close together to be viewed together. For example, two lines side by side within an analyte detection region or a picture formed from discrete lines can be interactive.

Thus the present invention provides an assay device which generates a signal indicative of the addition of a liquid to the device, the signal being formed irrespective of the presence of absence of the analyte of interest, and wherein the signal does not provide information as to whether a labelled antibody has been mobilised and permeated along a carrier in correctly functioning form.

Preferably, the assay device has a casing, the casing having a first window therein though which the test signal and sample presence signal are viewable, when formed. This window may delimit the analyte detection region, encouraging the user to view the contents of the window as forming an interactive symbol with a particular semantic meaning; for example, where a first combination of signals indicate a first outcome of the test and a second combination of signals indicate a second outcome of the test.

Preferably, the sample presence signal resembles a minus sign. Preferably, the sample presence signal is oriented parallel to the direction of flow of the liquid sample in the liquid transporting means. Preferably, the sample presence signal interacts with the test signal, to form a symbol (such as a "plus" sign) which represents a positive result when the analyte of interest is present. Typically, the test signal is in the form of an elongate patch orthogonal to the direction of fluid flow. Preferably, the test signal intersects the sample presence signal and so forms a plus sign when the test result is positive.

Preferably, the assay device further comprises a control signal generation means downstream of the analyte detection region adapted to generate a control signal indicative that one or more reagents present in the assay device are functioning. Where the assay device has a casing with a first window, the control signal generation means is preferably located in a second window.

The window may be any means through which the test signal and/or sample presence signal generation means can be viewed, for example an aperture. Such an aperture may be open or may have a transparent protective layer in, above and/or underneath the aperture.

The signal generated may be any such that a difference in reading may be easily and readily ascertained before and after the sample presence indicator means has been wetted with sufficient sample. Such means however should not interfere with the assay result itself.

Preferably, the liquid transporting strip comprises material which, when dry, is substantially opaque but which, when wet, becomes transparent. The liquid transport means may advantageously comprise several portions; for example, a wick portion for initially contacting the liquid sample and a porous nitrocellulose strip portion in fluid communication with the wick. Conveniently, in such a device, the analyte detection region and the sample presence signal generation means are located on the liquid transporting strip means.

Preferably, the liquid transport means comprises a liquid transporting strip, especially a strip of bibulous material; for example, a porous carrier, such as a nitrocellulose strip. Preferably, the liquid transporting strip comprises material which, when dry, is substantially opaque but which, when wet, becomes transparent. The liquid transport means may advantageously comprise several portions; for example, a wick portion for initially contacting the liquid sample and a porous nitrocellulose strip portion in fluid communication with the wick. Conveniently, in such a device, the analyte detection region and the control sample presence generation means are located on the liquid transporting strip means.

Preferably, the assay device has a surface visible to the user and the sample presence signal generation means comprises a coloured portion which is not on the surface visible to the user and which is overlaid by a material which, when dry, is substantially opaque and which initially obscures at least a part (preferably all) of the coloured portion (typically located within the aperture) but which, when wet, is sufficiently translucent or transparent to allow at least the initially obscured part of the coloured portion to become visible to the user. By "coloured" we mean that the coloured portion is any colour which is discernibly different, to a human observer, to that of the surrounding (and overlying) test strip when wet.

The embodiment defined in the previous paragraph enables a visible indication to be provided which is of particular convenience, as the shape, size, and colour of the coloured portion may readily be selected for any particular application. Thus, the coloured portion may be black or one or more colours, a shape or pattern, text, a message, or any other visible indication. A clear, unambiguous line or other shape can therefore be provided at any angle or orientation without fadeout.

Preferably, the strength or magnitude of the sample presence signal generation means is comparable to that of the test signal when a particular result, for example the presence of analyte, is determined. The fact that a coloured portion may be selected to have specified optical properties, such as one or more colours, a shape or pattern, text, a message, or any other visible indication, means that this aim can readily be achieved.

The coloured portion may be part of, or associated with, the liquid transporting strip, for example in the form of a prefabricated or imprinted layer, or a sheet applied or a block in contact with the liquid transporting strip or sufficiently close to the liquid transporting strip to be visible therethrough when the strip is rendered transparent by wetting. A sheet may be attached by adhesive, although in a preferred embodiment, the sheet is a plastics or other material portion pressed against the liquid transporting strip. The sheet may be pressed against the liquid transporting strip means by a protruberance from the assay device casing, which protruberance may be rigid or resiliently deformable.

In preferred embodiments, the liquid transporting strip comprises a nitrocellulose strip backed with a backing layer, such as mylar. Preferably, the coloured portion comprises a coloured piece of plastics material in contact with the nitrocellulose layer with the mylar layer being uppermost in the device window. The piece of plastics material may be part of the casing of the assay device.

Preferably, the coloured portion presses upon the liquid transporting strip means. It is perhaps surprising that this works as one would have thought it would interfere with liquid flow in the liquid transporting strip means.

Alternatively, the coloured portion may be printed on the backing layer. Alternatively, the coloured portion may be printed or otherwise formed on a sheet of mylar or other plastics material which is affixed to the side of the nitrocellulose strip not visible to a user; this may be the backing layer side but preferably the sheet is in direct contact with the nitrocellulose.

A line may be printed or otherwise formed or deposited on the side of the nitrocellulose strip that is not presented to the user using an ink which does not penetrate through the nitrocellulose strip.

The assay device may be of otherwise conventional construction, similar to that disclosed in EP 291194 or EP 560411.

The assay device will typically have a porous sample wick intended for the collection of the liquid sample which is in fluid connection with the liquid transporting strip means. Thus the sample collected by the porous sample wick flows on the liquid transporting strip means whereby it travels towards the analyte detection region.

The sample presence signal generation means alternatively comprises a mobilisable detectable material such as an ink spot or a coloured dye, which is localised on or in the liquid transport means and which when wetted by the liquid sample, is carried by it along the liquid transport means resulting in a streaked line generally parallel with the sample flow direction. This streaked line provides a "minus" sign and again is independent of any binding reaction and therefore not subject to any signal diminishment. Since the streaked line will continue to be formed along the liquid transport means as the liquid sample progresses, the control signal generation means, if present, may be offset from the flow path of the sample presence signal such that it does not interfere with the control signal.

The resulting coloured streak provides a visible indication to a user that sufficient liquid sample has been taken up. The mobilisable detectable material may comprise a coloured material such as an ink spot or a coloured dye, or a colour-forming material such as a pH indicator which changes colour or an enzyme which catalyses formation of a coloured material. Conveniently, only a localised patch or spot of coloured or colour-forming material may be located on the liquid transporting strip means, thereby simplifying manufacture.

Typically, the assay device will further comprise a window through which both the sample presence signal, such as a coloured streak, when formed, and the test result, when formed can be seen. Preferably, the patch or spot of coloured or colour-forming material is located outside of the window, so that the coloured or colour-forming material can only be seen once the streak has been formed. Alternatively, the patch or spot of coloured or colour-forming material may be obscured prior to use, e.g. by concealment beneath an opaque material such as an adhesive sheet or label or the like.

Preferably, the coloured or colour-forming material has appropriate properties and is present in an appropriate amount to give a coloured sample presence indicator or streak which is of similar visible appearance to the test signal when a positive test result is indicated.

A possible problem with such a device, if it also has a control signal generation means, downstream from the patch or spot of coloured or colour-forming material, is that the streak may continue to migrate into the control signal generation means, thereby causing a confusing additional signal to be formed offset from the flow path of the sample presence indicator streak. Such a problem is preferably solved by providing the control signal generation means offset from the streak. In a preferred embodiment, the localised patch or spot is centered on the liquid transporting strip means and the control signal generation region is off-centre. The control signal generation region may be in a window offset from the flow path of the sample presence indicator signal or streak.

In yet another embodiment, the sample presence signal generation means comprises a material immobilised thereon which is adapted to change a visual property in response to wetting.

Typically, the visual property which changes is the colour of the material.

The material may be adapted to change a visual property in response to wetting by any substance or, more preferably, in response to the presence of a liquid (e.g. a sample of interest) having specific properties.

Accordingly, the sample presence signal generation means can be shaped as is desired to give a particular indication. A suitable material is a solvatochromic dye, a pH indicator, or a chromoreactand. Such materials will change colour either in response to wetting, or to wetting with specific liquids or liquids with specific properties, such as polarity.

An example of a solvatochromatic dye is Reichardt's dye. Examples of suitable pH indicators are Bromocresol Green, Phloxine B, Quinalidine Red, Bromophenol Blue etc. In this respect reference is made to corresponding application no. EP 02250121.7, filed 9 Jan. 2002.

An indicator could be immobilised with a buffer or other substance e.g. acid or alkali to control its pH and hence its initial colour. The indicator would be selected such that it would change colour when contacted with the sample e.g. urine. A buffer or other compound e.g. acid or alkali could be added to the device upstream from the indicator that would be solubilised by the sample and ensure that the pH of the sample was such that a dramatic pH change and hence colour change occurred when the sample contacted the indicator.

Suitable indicators could be immobilised on the membrane by entrapping them within hydrophilic polymers such as Poly 2-Hydroxy ethyl methacrylate (poly(HEMA)) or poly Hydroxy Propyl Methacrylate (poly(HPMA)).

Alternatively it is possible to dye materials with indicators in such a way that the dye does not leach out when the material is wetted e.g. as is well known in the field of pH indicator papers or strips. This could be done by selecting a membrane and dye combination that interact in this way.

Alternatively a water insoluble dye could be applied in a solvent that is then evaporated off, leaving behind the water insoluble pH indicator dye. Alternatively, some indicator dyes can be fixed by heat or U.V. irradiation.

Alternatively a dye could be selected that binds to nitrocellulose via a hydrophobic interaction (in the same way that proteins bind to nitro-cellulose) or the indicator could be used to dye a carrier molecule (such as a protein or micro-sphere) that would itself bind to the nitro-cellulose.

BRIEF DESCRIPTION OF THE DRAWINGS

An example embodiment of the present invention will now be illustrated with reference to the follow Figures in which.

DETAILED DESCRIPTION OF THE EXAMPLE EMBODIMENTS

Example 1

Figure 1:
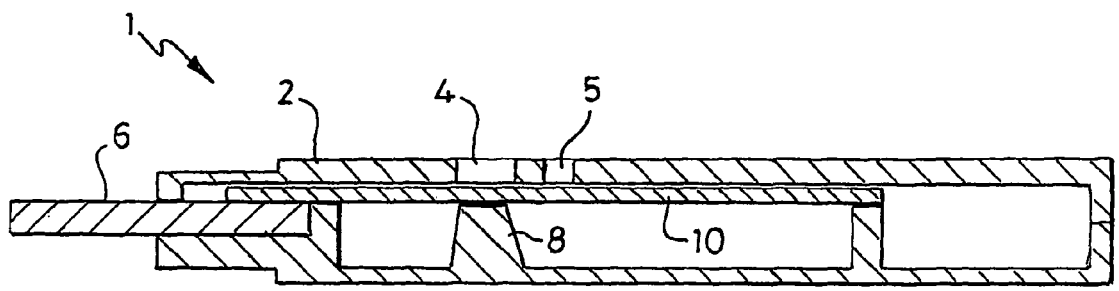
FIG. 1 is a cross section through an assay device according to the present invention.
Figure 2:
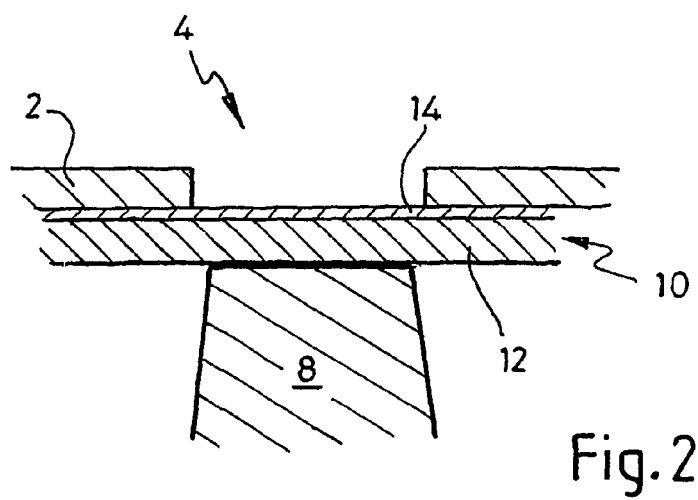
FIG. 2 is an enlarged view of part of the assay device shown in FIG. 1.

FIG. 1 is a cross section through an assay device 1 which measures urinary hCG, for use as a pregnancy test device. Assay device 1 comprises a case 2, made from a plastics material and having a result window 4 in the form of an aperture. A second aperture 5 through which a control signal generation means can be viewed is optional. A wick 6 protrudes from the case 2, for drawing up a liquid sample into the device, and a nitrocellulose strip 10 is in fluid communication with the wick 6. Case 2 has a protruberance 8 on an inner surface. Protruberance 8 presses against the nitrocellulose strip 10. FIG. 2 is an illustration of part of FIG. 1. This shows that the nitrocellulose strip 10 comprises an initially opaque porous nitrocellulose layer 12, backed by a transparent mylar layer 14.

Figure 3:
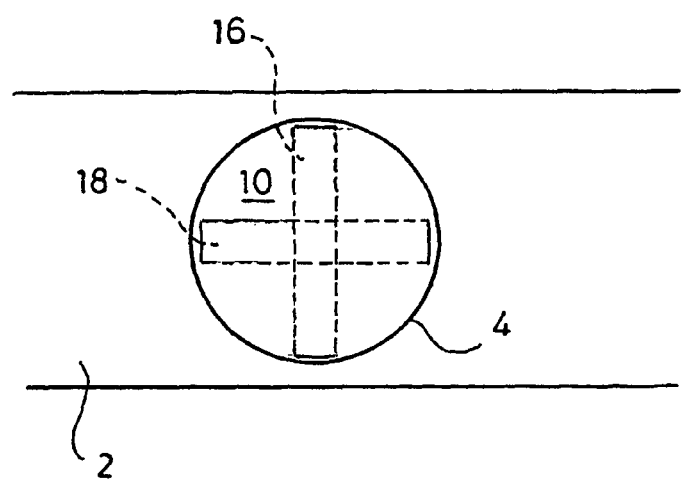
FIG. 3 is a plan view of part of the assay device of FIG. 1.

FIG. 3 is a plan view of the assay device shown in FIG. 1 (but to a different scale to FIG. 1), showing that a portion of the nitrocellulose strip 10 is visible through result window 4. Initially invisible, there are two regions which can be seen through the result window that may change colour during an assay. Firstly, there is an analyte detection region 16. Nitrocellulose strip 10 has a labelling region 20 (FIG. 1) in which mobile blue latex—labelled mouse anti-hCG antibodies are present. The analyte detection region 16 has immobilised anti-hCG antibodies.

Secondly, protruberance 8 (FIG. 2) is in the shape of an elongate thin bar, shown as 18, in FIG. 3. This is coloured blue, and presses against the nitrocellulose layer 12. It is initially invisible, as the nitrocellulose layer 12 is opaque when it is dry.

In use, the wick 6 of the assay device 1 is brought into contact with the fluid sample. In the present example, the fluid sample is urine. The liquid sample passes up the wick 6, by virtue of the wicking action of the wick. The liquid sample then passes along the porous nitrocellulose layer 12, where it carries along mobile labelled antibody from labelling region 20. As the fluid sample passes along the nitrocellulose strip, the liquid sample wets the nitrocellulose progressively. If hCG is present, the labelled anti-hCG antibodies form a sandwich complex with hCG, giving a visible test signal in the analyte detection region 16.

As the nitrocellulose strip is wetted, it becomes transparent revealing the blue colour of the protruberance 8. Therefore, sample presence signal generation means 18 reveals the protruberance 8, which is now visible and constitutes the sample presence signal.

If hCG is not present, the only visible signal apparent to an observer will be the colour of the protruberance 8. This sample presence signal on its own resembles a minus sign. When a sample containing hCG is applied, the analyte detection region 16 will change colour, by virtue of the retained labelled antibodies, giving the test signal. Therefore, the symbol apparent to the user will be a plus symbol, formed by both the test signal and the sample presence signal.

Therefore, the user can be confident that sufficient liquid has been added to the assay device and that the assay has given a positive result, which, in this case, indicates that the test subject is pregnant.

The colour of the protruberance 8 is selected so that it corresponds to the colour of the analyte detection region 16 when it gives a typical positive result. This is not only visually appealing, but gives an additional level of reassurance to the user.

FIGS. 8(a)-(d) are a series of photographic images showing (a) a test device, without top cover or nitrocellulose strip 10, in which a coloured plastic protruberance 8 formed in the bottom cover can be seen; (b) an assembled device having a result window 4 and, additionally, an end control window 36 the purpose of which is to provide a sample presence signal line by retaining labelled antibody in a conventional fashion.

Figure 8A:
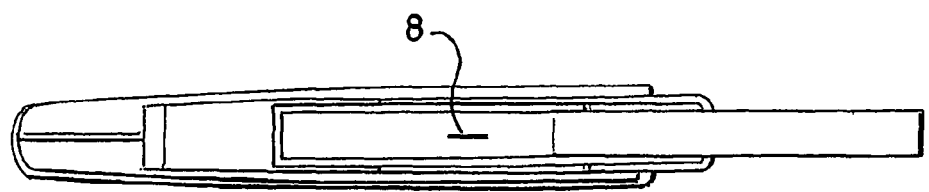
FIGS. 8(a)-(d) show photographic images of an assay device in accordance with the invention (a) without top cover or nitrocellulose strip, (b) in assembled form, (c) indicating that a sample is present, and (d) showing a positive result.
Figure 8B:
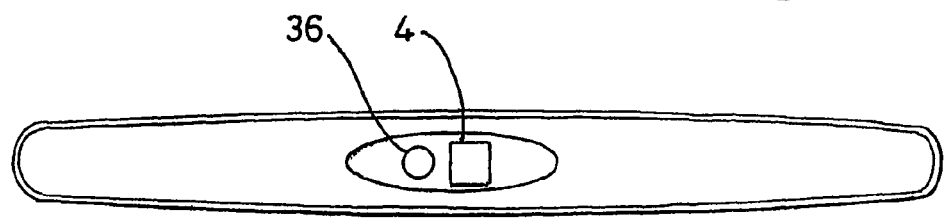
Figure 8C:
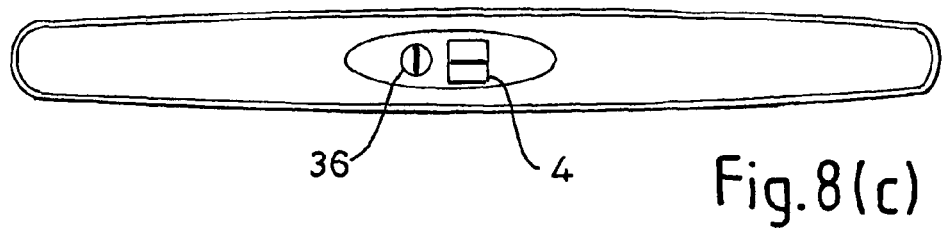

FIG. 8(c) shows the device after a test, when no positive result is indicated. As a result of the wetting of the nitrocellulose layer, which has become transparent revealing the protruberance 8, a minus sign appears in result window 4.

Figure 8D:
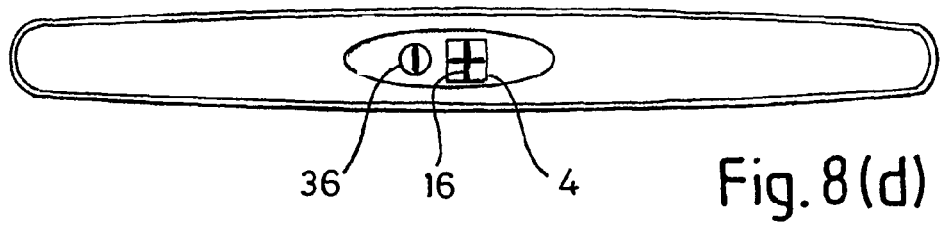

FIG. 8(d) shows device indicating a positive result due to the presence of analyte. Analyte detection region 16 has also changed colour, hence a plus sign is formed.

Example 2

Figure 4:
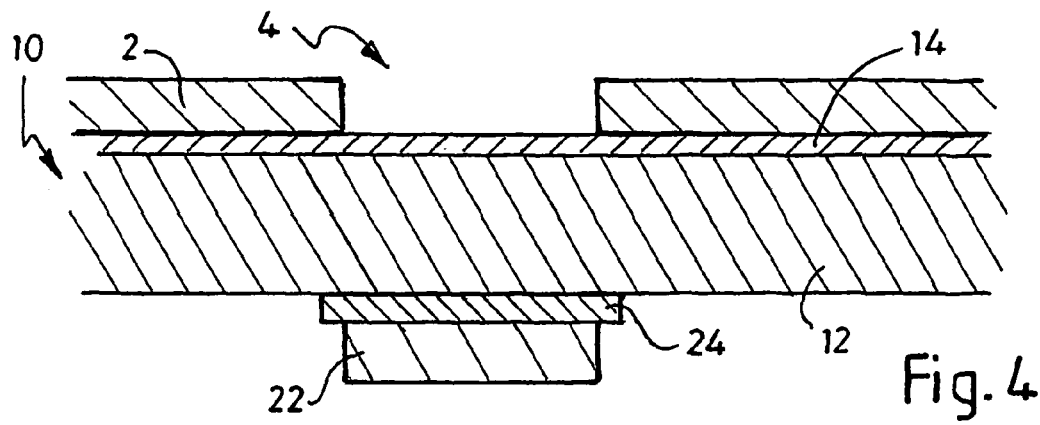
FIG. 4 is a cross-section through part of an assay device according to an exemplified embodiment of the invention.

FIG. 4 illustrates an example embodiment of the assay device. In this embodiment, a printed mylar layer 24 is applied to the nitrocellulose strip, in contact with the porous nitrocellulose layer 12. It is held in place by a protruberance 22 supported by the case 2 of the assay device 1. Conveniently, the use of a mylar strip 24 enables any type of image to be used merely by printing the image on the mylar strip with conventional printing technology.

Example 3

Figure 5:
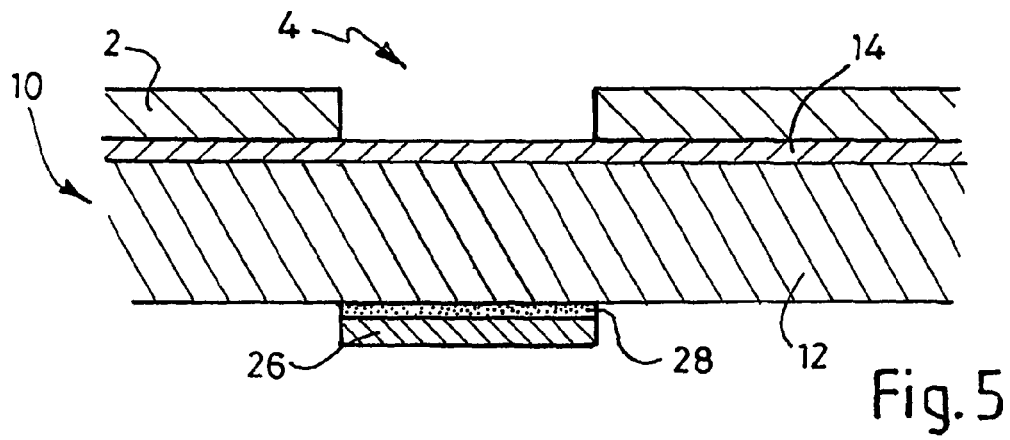
FIG. 5 is a cross-section through a part of a further exemplified assay device in accordance with the invention.

FIG. 5 illustrates an alternative embodiment in which a visible image is applied to a mylar layer 26 by means of printing, and the mylar layer is held in contact with the porous nitrocellulose layer 12 by an adhesive layer 28. No protruberance is required in this example, but can optionally be provided.

Example 4

Figure 6:
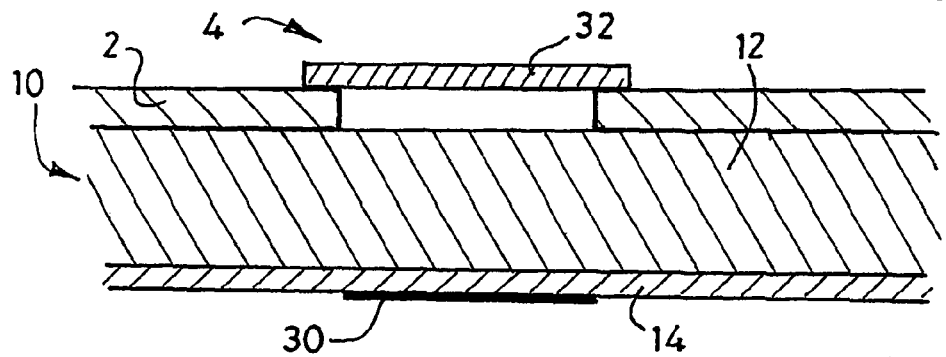
FIG. 6 is a cross section through a part of a further exemplified assay device in accordance with the invention.

FIG. 6 illustrates a further example embodiment in which the nitrocellulose strip 10 is inverted, with the mylar backing layer 14 away from the user. A coloured image is printed directly onto the mylar layer 14 and simply consists of ink 30 (thickness exaggerated in the Figure). In this embodiment, an additional protective layer 32 is provided to protect the nitrocellulose strip. This protective layer 32 is 50 microns thick Adhesives Research™ laminate, applied by a hand roller. This was found to slow down the movement of liquid through the laminated region which can be of benefit. Again, no protruberance is required but can optionally be provided.

Example 5

Figure 7:
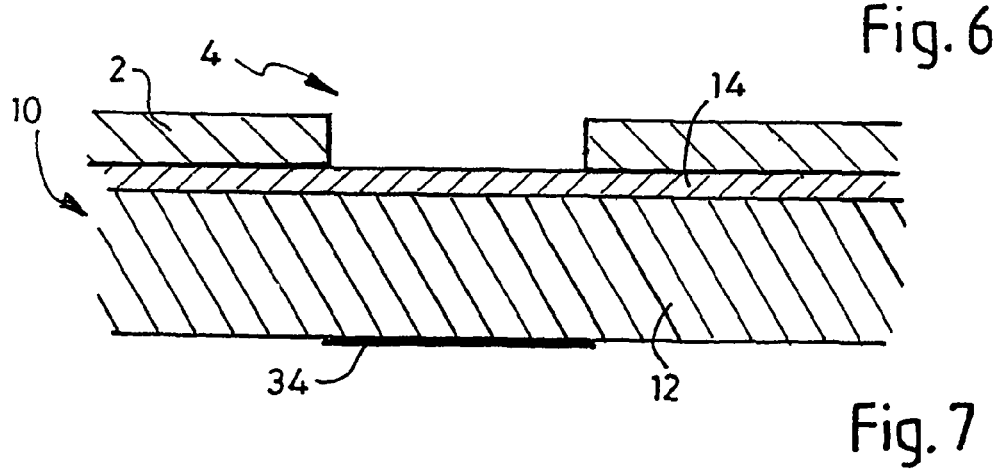
FIG. 7 is a cross section through a part of a still further exemplified assay device in accordance with the invention.

FIG. 7 illustrates a further example embodiment in which the nitrocellulose strip is orientated as before, with the mylar layer 14 towards the user. An ink layer 34 is printed directly onto the porous nitrocellulose layer 12. It is necessary that this ink does not penetrate through the nitrocellulose layer, and an appropriate ink must be selected for this purpose.

Example 6

FIG. 9 illustrates in plan view, a schematic of the nitrocellulose strip of an alternative embodiment. Here, the casing, wick, analyte detection region and label are as before. The nitrocellulose strip 100 is partly visible through a results window 110. An ink spot 120 is located on the nitrocellulose strip 100. It is not within the results window 110, and is therefore obscured initially by the assay device case (not shown).

In use, ink from the ink spot 120 is carried along by the flow of the liquid sample forming a streak 130 which is visible in the results window 110. The ink spot is made from an ink selected so that it is neither insufficiently mobile to produce a suitable streak, nor moves entirely with the solvent front so as to not form a streak.

Figures 9A, 9B, 9C:
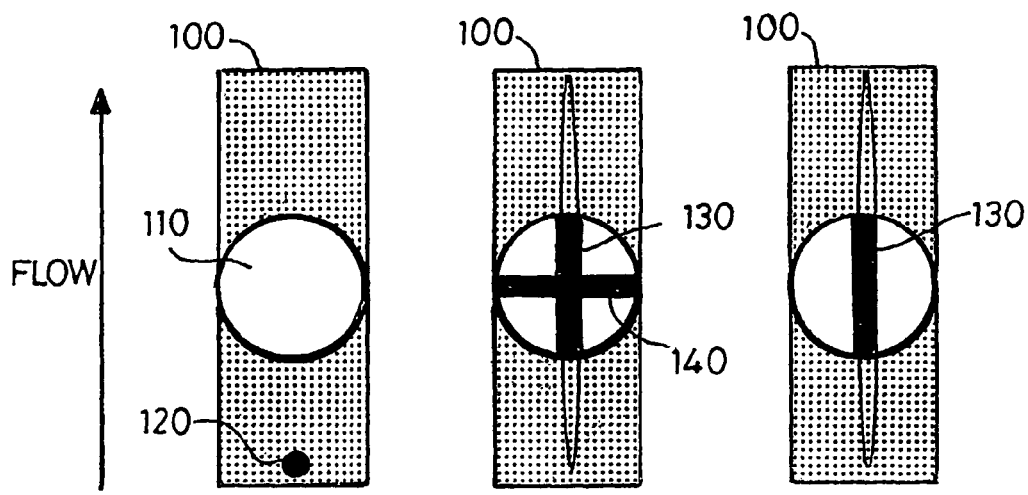
FIGS. 9(a)-(c) shows an assay device according to further embodiment of the invention, (a) before a measurement is made; (b) after a measurement is made, indicating a positive result; and (c) after contact with a liquid sample, not indicating a positive result.

However, a reaction zone having immobilised anti-hCG antibodies is also present, forming a coloured bar 140 indicative of a positive result, depending on the presence or amount of analyte in the liquid sample. Thus, in the event of a positive result, a plus sign is thereby produced, as shown in FIG. 9(b). FIG. 9(c) illustrates the coloured bar 140 on its own, when no positive results is indicated but liquid sample has been added.

Figure 10:
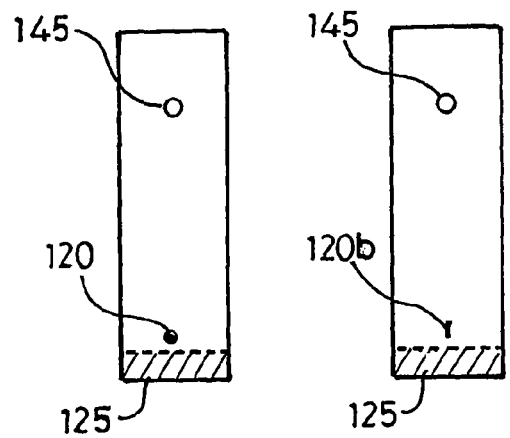
FIG. 10 is a plan view of the nitrocellulose strip of the assay device shown in FIG. 8(a)

FIG. 10 illustrates the nitrocellulose strip 100 for use in this invention. The ink spot 120 can be a circular spot, or a rectangular or other shaped mark 120b. The ink spot 120 is positioned downstream from a region 125 which, when the device is assembled, is in contact with the wick. Holes 145, in the nitrocellulose strip, are provided to engage with formations on the assay device case, holding the nitrocellulose strip in place.

A suitable ink can be applied using an Ostaline® rollerball 0.5 mm pen.

FIG. 11 shows the sequential development of the streak using this ink.

Example 7

Figure 12:
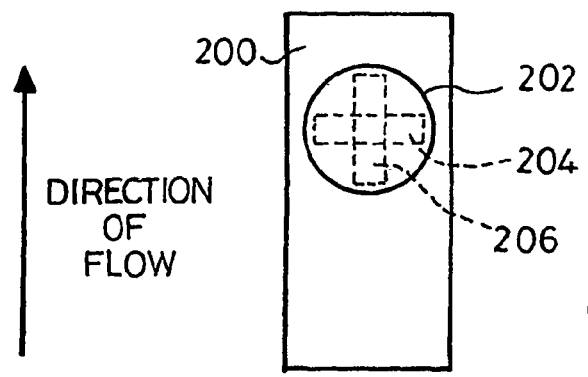
FIG. 12 is a plan view of a portion of an assay device in accordance with a further embodiment of the present invention.
Figure 11A:
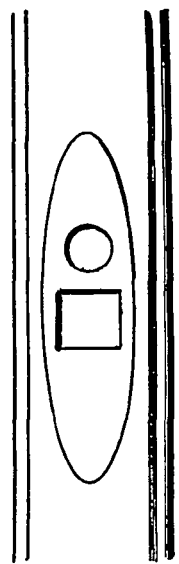
FIGS. 11(a) through 11(d) are photographs of sequential development of the sample present signal in the test device shown in FIGS. 9 and 10.
Figure 11B:
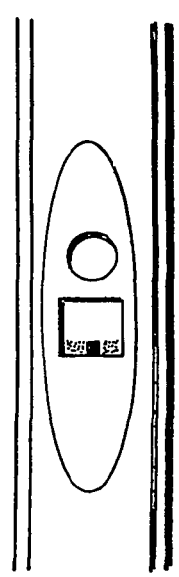
Figure 11C:
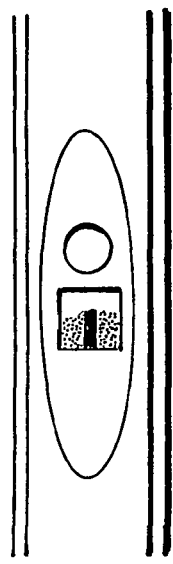
Figure 11D:
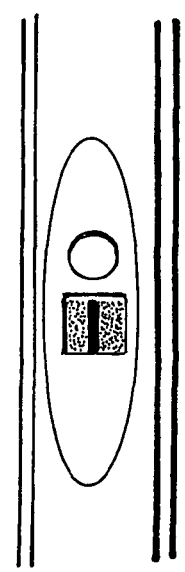

FIG. 12 illustrates the nitrocellulose strip of a further example device. As before, the nitrocellulose receives a liquid sample from a wick, and is enclosed within a case (not shown) having a results window 202 through which an analyte detection region, which is initially uncovered 204 can be viewed. There is additionally provided a sample presence signal generating region 206.

The sample presence signal generating region 206 comprises a material which changes colour in the presence of an appropriate liquid sample. For example, a pH indicating dye, for example, bromocresol green applied in a matrix of cross-linkable poly hydroxy ethyl methacrylate (poly(HEMA)).

Further modifications and alternations may be made within the scope of the invention herein described.

The invention claimed is:
1. An assay device for detecting an analyte in a liquid sample, the assay device comprising:
   a casing, the casing comprising at least one window;
   a labeling region, the labeling region comprising a mobilisable labeled binding agent; and
   a nitrocellulose strip located within the casing, the nitrocellulose strip being substantially opaque in a dry state and being translucent when contacted by the liquid sample, the nitrocellulose strip comprising:
   (i) an analyte detection region comprising an immobilized binding agent which binds the analyte, the analyte detection region located downstream of the labeling region, wherein the analyte detection region is visible through the at least one window;
   (ii) a printed line located on the lower surface of the nitrocellulose strip in the analyte detection region, wherein the printed line is on the side of the nitrocellulose strip that is not visible through the at least one window when the nitrocellulose strip is in a dry state;
   (iii) a control region that is off-center from the flow path, the control region located downstream of the analyte detection region; wherein the control region is visible through the at least one window; and
   (iv) a sample presence indicator line, wherein said line is oriented substantially parallel with the direction of flow of the liquid sample;
   wherein in use, the liquid sample contacts and migrates along the nitrocellulose strip, and wherein the printed line is visible to a user through the at least one window when the nitrocellulose strip is translucent.
2. The assay device of claim 1, wherein when analyte is present in the sample, analyte binds to the mobilizable labeled binding agent and the immobilized binding agent to form a test signal in the analyte detection region of the nitrocellulose strip.

3. The assay device of claim 2, wherein the line and the test signal form a symbol representative of a positive result in the presence of analyte.

* * * * *